United States Patent
Koshti et al.

(10) Patent No.: US 9,308,156 B2
(45) Date of Patent: Apr. 12, 2016

(54) BLENDS OF O-ACYL-ISETHIONATES AND N-ACYL AMINO ACID SURFACTANTS

(71) Applicant: GALAXY SURFACTANTS LTD., Navi Mumbai (IN)

(72) Inventors: Nirmal Koshti, Piscataway, NJ (US); Bhagyesh Jagannath Sawant, Kalyan (IN)

(73) Assignee: GALAXY SURFACTANTS LTD., Maharashtra (IN)

(*) Notice: Subject to any disclaimer, the term of this patent is extended or adjusted under 35 U.S.C. 154(b) by 0 days.

(21) Appl. No.: 14/435,267

(22) PCT Filed: Aug. 12, 2013

(86) PCT No.: PCT/IN2013/000494
§ 371 (c)(1),
(2) Date: Apr. 13, 2015

(87) PCT Pub. No.: WO2014/181342
PCT Pub. Date: Nov. 13, 2014

(65) Prior Publication Data
US 2015/0250694 A1    Sep. 10, 2015

(30) Foreign Application Priority Data
May 8, 2013  (IN) .......................... 1669/MUM/2013

(51) Int. Cl.
*C11D 1/37* (2006.01)
*A61K 8/44* (2006.01)
*A61K 8/46* (2006.01)
*C11D 3/34* (2006.01)
*A61Q 19/10* (2006.01)
*A61K 8/41* (2006.01)

(52) U.S. Cl.
CPC . *A61K 8/466* (2013.01); *A61K 8/41* (2013.01); *A61K 8/44* (2013.01); *A61Q 19/10* (2013.01); *C11D 1/37* (2013.01); *C11D 3/349* (2013.01); *A61K 2800/596* (2013.01); *A61K 2800/75* (2013.01); *A61K 2800/80* (2013.01)

(58) Field of Classification Search
CPC ........... C11D 1/37; C11D 3/349; A61K 8/466
See application file for complete search history.

(56) References Cited

U.S. PATENT DOCUMENTS

| | | | |
|---|---|---|---|
| 2,729,657 | A | 1/1956 | Krems |
| 4,455,263 | A | 6/1984 | Noble |
| 5,186,855 | A | 2/1993 | Crudden |
| 5,372,751 | A | 12/1994 | Rys-Cicciari et al. |
| 5,393,466 | A | 2/1995 | Ilardi et al. |
| 5,415,810 | A | 5/1995 | Lee et al. |
| 5,496,959 | A | 3/1996 | Day |
| 5,612,307 | A | 3/1997 | Chambers et al. |
| 5,681,804 | A | 10/1997 | Hamada et al. |
| 5,837,668 | A | 11/1998 | Tracy et al. |
| 5,925,603 | A | 7/1999 | D'Angelo |
| 5,965,500 | A | 10/1999 | Puvvada |
| 6,057,463 | A | 5/2000 | Tracy et al. |
| 6,998,113 | B1 | 2/2006 | Traynor et al. |
| 7,001,592 | B1 | 2/2006 | Traynor et al. |
| 7,025,952 | B1 | 4/2006 | Traynor et al. |
| 7,037,513 | B1 | 5/2006 | Traynor et al. |
| 7,226,581 | B2 | 6/2007 | Traynor et al. |
| 7,226,582 | B2 | 6/2007 | Traynor et al. |
| 7,879,780 | B2 | 2/2011 | Tsaur |
| 8,114,824 | B1 | 2/2012 | Dasgupta et al. |
| 8,263,538 | B2 | 9/2012 | Tsaur et al. |
| 8,268,767 | B2 | 9/2012 | Tsaur et al. |
| 2009/0062406 | A1 | 3/2009 | Loeffler |
| 2013/0189212 | A1 | 7/2013 | Jawale et al. |

FOREIGN PATENT DOCUMENTS

EP    0964674    12/1999
WO    2014030038    9/2012

OTHER PUBLICATIONS

"Assessment Plan for Fatty acids, coca, Zsulfoethyi esters, sodium salts (Sodium Cocoyl Isethionate; CAS #61789-32-0)", Prepared for the Sodium Ethyl Sulfonates Coalition, Nov. 24, 2006, Keller and Heckman LLP, [http://www.epa.gov/chemrtk/pubs/summaries/ftyacdc2/c16590tp.pdf] downloaded on Apr. 8, 2015.
"International Search Report for PCTIN2013/000494 dated Apr. 8, 2014".
Friedman, "Chemistry, Formulation, and Performance of Syndet and Combo Bars", Soap Manufacturing Technology, AOCS Meeting, Oct. 1997, pp. 153-156.
Sun, et al., "Solubilization of sodium cocyl isethionate", J. Cosmet. Sci., 54, 559-568 (Nov./Dec. 2003).

*Primary Examiner* — Robert Havlin
(74) *Attorney, Agent, or Firm* — Kramer & Amado, P.C.

(57) ABSTRACT

The present invention discloses a process for preparing blends of O-acyl isethionates and N-acyl amino acid surfactants using common fatty acid chlorides, in quantitative yields. The blends are in liquid form or can be spray dried to obtain solid dried form.

8 Claims, 2 Drawing Sheets

US 9,308,156 B2

BLENDS OF O-ACYL-ISETHIONATES AND N-ACYL AMINO ACID SURFACTANTS

FIELD OF INVENTION

The present invention relates to a cost-effective process for the manufacture of homogeneous blends of O-acyl isethionates (Formula I) and N-acyl amino acid surfactants (Formula II) wherein, R is selected from $C_5$ to $C_{21}$ saturated or unsaturated alkyl group, $R_1$ represents H, or small alkyl chains ranging from $C_1$ to $C_4$, $R_2$ represents H or all groups on a carbon of natural amino acids, $R_3$ represents an acidic group such as carboxyl or sulphonyl with a counter cation of alkali metals as in COOX, $CH_2\_SO_3X$, where $X=Li^+$, $Na^+$ or $K^+$, $R_4$ is H or methyl and M is a cation selected from $Na^+$, $K^+$, $NH_4^+$ or a quaternary ammonium cation derived from tertiary amines, from the same fatty acid chlorides in quantitative yields. More particularly, the present invention relates to a process for the preparation of O-acyl isethionates by reacting alkali metal or ammonium salts of hydroxyalkyl sulphonates with fatty acid chloride followed by the reaction of the remainder fatty acid chloride with equivalent quantity of aqueous solution of one or more amino acids in the presence of a base in the aqueous medium to give a mixture of anionic surfactants, namely, O-acyl isethionates (Formula I) and N-acyl amino acid surfactants (Formula II) in any desired ratio.

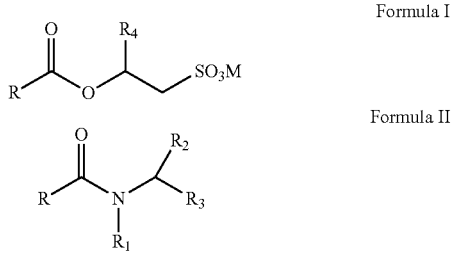

Formula I

Formula II

BACKGROUND OF INVENTION

Personal cleansing compositions of today are designed to give good cleansing effect in addition to other benefits such as moisturization to the skin. In order to achieve superior cleansing and moisturizing skin benefit, traditionally, very high levels of occlusive agents like petrolatum have been used. For example, Dove Cream Oil (Unilever) and Olay Ribbon body washes (Proctor and Gamble) employed as high as 30% of emollient oils. There have been continuous efforts to provide skin and hair care benefits from cleansing compositions through actives like silicone oil, petrolatum and a variety of triglycerides. Some cleansing compositions have been reported to use as high as 50% of emollients. (Chambers et al. U.S. Pat. No. 5,612,307 and Pavvada et al. U.S. Pat. No. 5,965,500).

Recently Tsaur et al. have revolutionized cleansing technology by inventing various combinations of mild surfactants. U.S. Pat. No. 8,263,538 teaches a combination of N-acyl amino acid surfactants, such as sodium N-cocoyl glycinates and sodium N-cocoyl sarcosinates, with amphoteric/zwitterionic surfactants for 'super mild' personal cleansing compositions that showed total irritation score using patch test methodology to be less than 75% relative to 0.5% aqueous sodium dodecyl sulphate solution.

Yet another recent patent by the same group (Tsaur et al. U.S. Pat. No. 8,268,767) reports combinations of cleansing surfactants that not only cleanse and deliver the benefit agents but are 'super mild' to skin. The said compositions comprise of both O-acyl isethionates and N-acyl amino acid surfactants for liquid cleansers of both skin and hair. The compositions are said to be 'super-mild' to skin when tested by standard patch test method on human volunteers. The above mentioned patent also reveals exceptionally mild compositions that deliver the occlusive moisturizers very effectively. Similarly, U.S. Pat. No. 8,114,824 discloses compositions with O-acyl isethionates and N-acyl amino acid surfactants that could accommodate maximum amount of moisturizer. In summary, the surfactant systems comprising of O-acyl isethionates and N-acyl glycinates or N-acyl sarcosinates as main ingredients have been reported to be very good cleansing systems that are 'super mild/gentle' on skin and excellent delivery vehicles of actives (benefit agents like emollients, silicones, triglycerides and petrolatum). The above mentioned patents teach that the 'super mildness' and 'delivery benefits' are obtained due to the exceptional synergy exhibited by the combination of these two classes of mild surfactants, namely, O-acyl isethionates (Formula I) and N-acyl amino acid surfactants (Formula II).

Out of these mild surfactants, N-acyl aminoacid surfactants, namely, alkali metal or ammonium salts of N-acyl glycinates, sarcosinate, taurates, glutamates, alanates etc are commercially available in solid form as well as in the form of aqueous solution for the formulators since they are highly water soluble. However, contrary to this, the corresponding N-acyl isethionates exhibit virtually no solubility in water. For example, sodium cocoyl isethionate has 0.1% solubility in water at 25° C. (Assessment Plan for Fatty acids, coco, sulfoethyl esters, sodium salts (sodium cocoyl isethionate prepared by Keller and Heckman LLP, November 2006). In addition, all alkali metal O-acyl isethionates have very high melting points of over 200° C. Incorporation of extremely high melting alkali metal O-acyl isethionates in personal care formulations (body wash, face wash) necessarily involves heating of the formulations which is sometimes not advisable due to thermo-susceptibility of other sensitive ingredients in addition to expending the energy for heating the entire mass. To overcome this difficulty of incorporation of alkali metal O-acyl isethionates in their solid form, researchers have created formulator-friendly 'Liquid Delivery Systems' (LDS) wherein alkali metal salts of O-acyl isethionates are solubilized in aqueous medium with the help of other surfactants and hence remain fluid and easy to incorporate (cold mixing) in the personal care formulation. EP0964674 A2 and U.S. Pat. No. 5,925,603 (Rhodia, Paul D'Angelo) report concentrated 'Liquid Delivery Systems' where in O-acyl isethionates are dispersed with alkyl imidazoline amphoteric surfactants and with anionic surfactants. US Patent application 20090062406 and U.S. Pat. No. 5,415,810 (Clariant, Matthias Loeffler) teach aqueous concentrated blends wherein O-acyl isethionates are made deliverable with N-acyl taurate and betaines. U.S. Pat. No. 7,879,780 reports stable cleansing compositions with O-acyl isethionates with betaines and sulphosuccinates. A recent patent application by Galaxy Surfactants reports liquid delivery systems for O-acyl isethionates using N-acyl glycinates and alkyl betaines (U.S. patent application Ser. No. 13/749,458, A Jawale et al.). The examples of commercially available 'liquid delivery systems' for sodium cocoyl isethionate are 1) Chemoryl™SFB, Lubrizol (sodium cocoyl isethionate, laureth sulphosuccinate and cocomidopropyl betaine), 2) Hostapon SCB, Clariant (sodium cocoyl isethionate, cocobetaine and 3) Miracare Plaisant, Rhodia (sodium cocoyl isethionate, cocoamphoacetate, and sodium cocoyl taurate).

All liquid delivery systems (LDS) that have been reported so far basically use other anionic or amphoteric/zwitterionic surfactants ('Solubilization sodium cocoyl isethionate'; J. Z Sun, M. C. E. Erickson, and J. W. Paar, J. Cosmetic Science 54, 559-568, 2003) to covert solid alkali metal O-acyl isethionates into either soluble or dispersible in aqueous medium. The biggest disadvantage of these 'liquid delivery systems' are that they are based on SOLID form of salts of O-acyl isethionates that are available in the form of needles, pastille, powder or granules. Making solid form of O-acyl isethionates itself involves a reaction at 225° C. and handling of molten mass to convert that into solid of desired physical form. These liquid delivery systems of O-acyl isethionate are created to ease the job of personal care formulators. However, the manufacturers of liquid delivery systems have to deal with dissolution of hard, virtually water-insoluble, high-melting (above 200° C.) O-acyl isethionates. This is achieved by heating and mixing of solid O-acyl isethionates with other surfactants, either anionic or amphoteric or both. Industrial process for manufacturing O-acyl isethionate involves very high temperature of 200 to 240° C. wherein fatty acid is reacted with alkali metal salts of hydroxyl ethyl sulphonate (Friedman, M. 2004. Chapter 5: Chemistry, Formulation, and Performance of Syndet and Combo Bars. In, Spitz, L. (ed), SODEOPEC Soaps, Detergents, Oleo-chemicals, and Personal Care Products, AOCS Press, Champaign, Il). The typical industrial procedure involves use of at least 1.4 to 2.0 molar equivalence of fatty acids with respect to alkali metal isethionate (40 to 100% excess of fatty acid) to effect the acid catalyzed esterification. The excess fatty acid is recovered after the desired degree of esterification. This process is known as DEFI (directly esterified fatty acyl isethionate) in literature. The esterification between hydroxyl ethyl sulphonate and fatty acid is effected at temperatures above 200 to 225° C. and excess fatty acid is typically recovered at a temperature of more than 200° C. under high vacuum. The recovery of fatty acid is never completely done and hence commercially available alkanoyl isethionates (O-acyl isethionates) are about 65 to 85% purity. Some amount of fatty acid (10 to 15% w/w of the final composition) needs to be left in the reaction mass so that the reaction mass with 65 to 85% O-acyl isethionate remains fluid at 200 to 240° C. This facilitates the transfer and conversion of molten mass into needles or prills by complex technology to ensure there is no deterioration of bulk of the molten mass at very high temperature. With every form of solid form (granule, powder or prill) of O-acyl isethionate that is produced there is a certain degree of dusting associated and that warrants special precaution as inhalation of this dust is a serious health hazard. Since the O-acyl isethionates are very high melting compound and virtually no solubility in water, these anionic surfactants are difficult to incorporate in personal care formulations. Thus, the Liquid Delivery Systems use commercially available solid form of O-acyl isethionates and convert solid O-acyl isethionates in liquid/fluid deliverable form using other surfactants. Another major disadvantage of the liquid carrier systems for O-acyl isethionates is that commercially available and patented LDS come with significant amount of certain surfactants. This restricts the usage of so called 'liquid delivery systems' since a formulator may not want to have the other surfactants that are used to create liquid deliverable O-acyl isethionate systems. The marketed 'liquid delivery systems come with imidazoline amphoterics or alkyl betaines or even anionics like fatty alcohol ether sulphates and the amount of these surfactants that are employed are too high relative to the amount of O-acyl isethionates that is solubilized or dispersed in water. In addition, surfactants like fatty alkyl betaines (used by Galaxy Surfactants and Clariant) are very expensive since they are made from an expensive raw material in the form of tertiary fatty amines with one long chain and two short alkyl chains on the tertiary nitrogen. Finally, liquid carrier systems comprising only combinations of 'super-mild' O-acyl isethionates and N-acyl amino acid surfactants have not been reported so far. The obvious reason is that by using solid form of O-acyl isethionates it not possible to create fluid and stable systems. For example, it is not possible to create aqueous homogeneous solution of sodium cocoyl isethionate and sodium cocoyl glycinate in 1:1 molar ratio from commercially available solid form of sodium cocoyl isethionate.

In view of O-acyl isethionates and N-acyl amino acid surfactants being the core of 'super mild' personal cleansing systems there is a need in the art 1) to make compositions using only these two 'super-mild' surfactants that are easy to incorporate in personal care formulations and 2) with an elegant process of manufacture that would have the flexibility of changing the ratio of O-acyl isethionates to N-acyl amino acid surfactants.

Object of Invention i) Accordingly, it is an objective of the present invention to develop a convenient, simple, energy efficient process that would have the capability to create blends of two types of surfactants that have been established as 'super-mild' in combination, namely, O-acyl isethionates (Formula I) and N-acyl amino acid surfactants (Formula II) from a common raw material, fatty acid chloride without addition of third surfactant.
ii) It is another objective of the present invention to develop a process that would have the flexibility of creating 'super-mild' blends of surfactants in varying ratio of O-acyl isethionates and N-acyl amino acid surfactants.
iii) It is also an objective of this invention to create a 'Liquid Deliverable System' for alkali metal salts of O-acyl isethionates that are otherwise insoluble in water and tough to formulate.
iv) It is also an object of the invention to prepare blends in the solid form for certain applications where water is to be avoided.

SUMMARY OF INVENTION

The present invention discloses a process of producing blends of O-acyl isethionates of Formula I, and N-acyl amino acid based surfactants of Formula II,

Formula I

Formula II wherein, R is selected from $C_5$ to $C_{21}$ saturated or unsaturated alkyl group, $R_1$ is selected from H, $C_1$ to $C_4$ alkyl, $R_2$ is selected from H or all groups on a carbon of natural amino acids, $R_3$ is selected from COOX, $CH_2\_SO_3X$, where X is selected from $NH_4^+$, $Li^+$, $Na^+$ or $K^+$, $R_4$ is H or methyl and M is the cation selected from $Na^+$, $K^+$, $NH_4^+$ or a quaternary ammonium derived from tertiary amines, the process comprising steps of A) reacting more than one equivalence of fatty acid chloride with alkali metal or ammonium salts of hydroxyalkyl sulphonates at 50 to 70° C. to obtain compounds of Formula I and B) reacting the product of step (A) (containing the remainder unreacted fatty acid chloride) with equivalent quantity of an aqueous solution of one or more amino acids and aqueous solution of a base under typical aqueous Schotten Baumann reaction conditions maintaining pH between 9 to 10.5 and at temperature of less than 50° C. to form compounds of Formula II.

Thus the present patent invention provides a novel process of producing a blend of aqueous O-acyl isethionates and N-acyl amino acid surfactants from same fatty acid chloride by reacting with alkali metal isethionate first and then with one or more than one amino acids in a sequential manner. The present invention offers an easy to formulate blend of O-acyl isethionates with any N-acyl aminoacid surfactants. The 'liquid deliverable systems' of O-acyl isethionates in combination with N-acyl aminoacid surfactant in any ratio can be obtained by the process of the present invention without the intermediacy of third surfactant as reported in the prior art.

The O-acyl isethionates for Formula I and N-acyl amino acid surfactants of Formula II, when blended together, are reported to produce 'super-mild' personal cleansing compositions. The present invention teaches a cost-effective and very 'easy to process' method of manufacture of creating blends of different ratios of the said 'super-mild' surfactants.

The above described features and advantages of the present disclosures will be appreciated and understood by those skilled in the art from the detailed description and the claims.

DETAILED DESCRIPTION OF INVENTION

The present invention describes an eco-friendly and cost-effective process for the manufacture of blends of mild surfactants O-acyl isethionates of Formula I and N-acyl amino acid surfactants of Formula II in varying ratios. These two categories of mild cleansing agents when blended together offer 'super-mild' cleansing compositions (U.S. Pat. Nos. 8,268,767; 8,114,824, and 8,263,538).

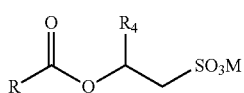

Formula I

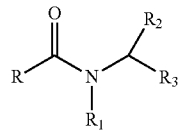

Formula II

The method of manufacture of the present patent application is amenable to production of 'super-mild' blends using the same starting material of fatty acid chloride for synthesis of both types of mild surfactants in two step procedure. The process described in this patent application is highly energy efficient and allows flexibility of controlling the ratio of O-acyl isethionates to N-acyl amino acid surfactants. The yields are quantitative and the process does not generate any waste. Finally, in addition to creating the established 'super-mild' blends of O-acyl isethionates and N-acyl amino acid surfactants for personal cleansing, the process delivers otherwise extremely difficult to incorporate, commercially available solid form, of alkali metal O-acyl isethionates in liquid form for easy incorporation into personal care formulations. (Solid forms of O-acyl isethionates are converted into 'Liquid Delivery Systems' as reported in U.S. Pat. Nos. 5,925,603, 5,415,810 and 7,879,780). It important to note that the unlike all the 'Liquid Delivery Systems' of O-acyl isethionates reported in literature (patented and commercially available, see section of the prior art) so far, the LDS of the present invention is made up of only two components, namely O-acyl isethionates and N-acyl amino acid surfactants. These two classes of surfactants are the core of 'super-mild' (U.S. Pat. No. 8,268,767) personal cleansing systems.

Thus, the present invention teaches the manufacture of 'super-mild' blends of O-acyl isethionates of Formula I and N-acyl amino acid based surfactants of Formula II

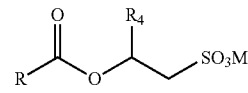

Formula I

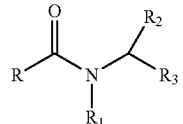

Formula II wherein, R represents alkyl chain, saturated or unsaturated, with carbon atoms ranging from $C_5$ to $C_{21}$, $R_1$ represents H, or small alkyl chains ranging from $C_1$ to $C_4$, $R_2$ represents H or all groups on α carbon of natural amino acids, $R_3$ represents an acidic group such as carboxyl or sulphonyl with a counter cation of alkali metals as in COOX, $CH_2\_SO_3X$, where $X=Li^+$, $Na^+$ or $K^+$, $R_4$ is selected from H or methyl and M is a cation selected from $Na^+$, $K^+$, $NH_4^+$ or a quaternary ammonium cation derived from tertiary amines.

Figure 1:
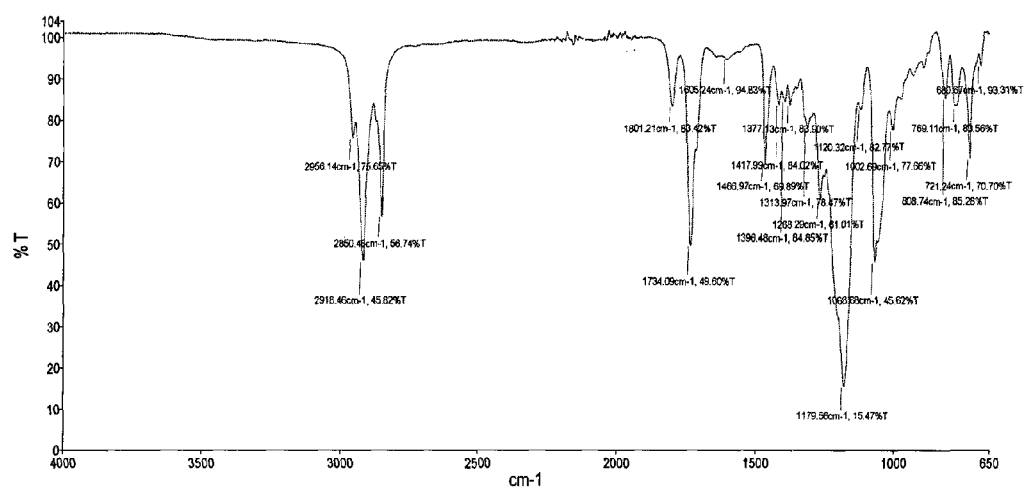
FIG. 1 shows FTIR of the first stage of the reaction, wherein, disappearance of hydroxyl stretching frequency of hydroxyl ethyl isethionate at 3400 cm-1 and simultaneous appearance of carbonyl stretching frequency of the ester group (O-acyl isethionate) at 1734 cm-1 and excess fatty acid chloride shows its carbonyl stretch at around 1800 cm-1.

The process of the present patent application involves a 'two-step' synthesis of the blends wherein the steps are performed sequentially. A mixture of powdered alkali metal or ammonium salts of hydroxyalkyl sulphonates (one equivalence) and fatty acid chloride (more than one equivalence) is stirred under slow nitrogen purging at 50 to 70° C. for about 3 to 4 hours (Scheme 1). The gaseous hydrochloric acid which is driven out by slow nitrogen purging is absorbed by an alkali trap. The progress of the reaction is monitored by disappearance of hydroxyl stretching frequency of hydroxyl ethyl isethionate at 3400 cm$^{-1}$ and simultaneous appearance of carbonyl stretching frequency of the ester group at 1734 cm$^{-1}$ in FTIR. The excess fatty acid chloride shows its carbonyl stretch at around 1800 cm$^{-1}$ in FTIR. (as shown in FIG. 1)

In about 3 to 4 hours, fatty acid chloride equivalent to alkali metal or ammonium salts of hydroxyalkyl sulphonates, reacts and the reaction mass is cooled to room temperature. Thus, the fluid, slightly pasty reaction mass obtained at this stage (step 1, Scheme 1) contains O-acyl isethionate and excess of unreacted fatty acid chloride (one or more than one or less than one equivalence depending upon initial stoichiometry). This stoichiometric excess of fatty acid chloride in the first step acts as a medium so that the reaction with solid alkali metal salt hydroxylalkyl sulphonate can be conducted at temperatures of less than 70° C. with quantitative conversion. Typically, the first step of esterification (Scheme 1) completes within 3 to 4 hours at 50 to 70° C. as monitored by FT Infrared spectroscopy. The excess fatty acid chloride of the first step is the reactant for the second step, the Schotten-Baumann reaction with the amino acids in the presence of a base (step 2, Scheme 1).

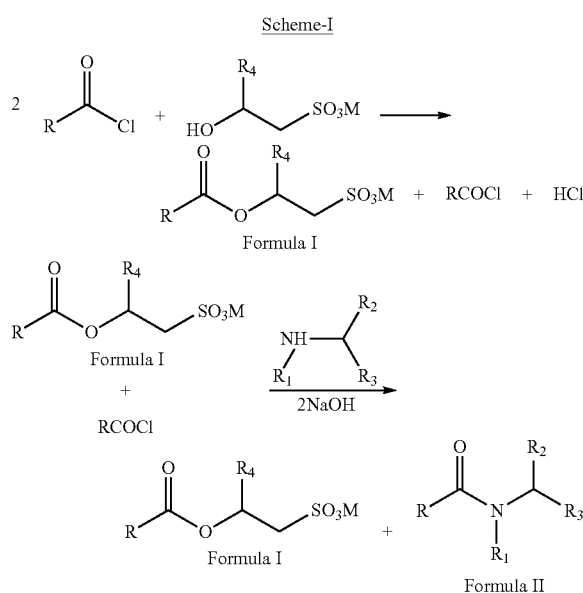

The excess amount of fatty acid chloride keeps the reaction mass containing stoichiometric quantity of O-acyl isethionate, fluid enough for the next step. For the second step of N-acylation of amino acid the fluid pasty reaction mass of the first step is added to a stirred mass of an amino acid (equivalence of amino acid depends on the excess fatty acid chloride depending upon the original stoichiometry of the first step) in water (quantity depends on the final solids content desired) under nitrogen at around 30 to 35° C. while maintaining pH of the reaction mass between 9.0 to 10.5 with simultaneous addition of alkali (two equivalence with respect to amino acid or fatty acid chloride) usually as 25% or 48% aqueous solution (e.g. sodium or potassium hydroxide) as depicted in Scheme 1. The reaction of unreacted fatty acid chloride in the fluid pasty mass of step 1 of Scheme 1 is reacted under typical conditions of Schotten-Baumann reaction (U.S. Pat. No. 2,527,657). Schotten-Baumann reaction is effected at temperatures ranging from 20 to 50° C. The preferred temperature range is between 20 to 35° C. For Schotten-Baumann condensation, pH range is important for achieving maximum yield. Generally, the N-acylation of amino acid can be very easily performed at pH ranging from 9.0 to 10.5. However, the preferred pH range for N-acylation of amino acid is from 10.0 to 10.5. After the simultaneous addition of thin fluid paste of step 1 (containing excess of fatty acid chloride and O-acyl isethionate) and two equivalence of alkali solution, the reaction mixture is stirred for additional 3 to 4 hours. Finally, pH of reaction mass is adjusted with a small quantity of mineral acid (hydrochloric acid) between 7.0 to 8.0 and with 30 to 40% of solids content. The solids content of the blend of mild surfactants is adjusted to desired level. Preferred range of solid content with good flowability of the final product is 30 to 40% (Example 10 and 11). However, blends with higher solids (>40%) are also possible. At higher solids level, instead of clear solution, generally pasty (high viscosity 1000 cps to 10 cps, yet fluid at room temp) product is obtained and this behavior depends on the constituents of the blend and the ratio of O-acyl isethionate and N-acyl amino acid surfactants.

The stoichiometry of unreacted fatty acid chloride at the end of the first step of O-acylation to amino acid used in the second step of N-acylation can vary from 1:1 to 1:1.10 on molar basis. Preferred excess of amino acid is around 3.0 to 5.0 mole %. Example 1 illustrates synthesis of blend of 'super-mild' surfactants in the ratio of 1:2 (sodium cocoyl isethionate (SCI):sodium cocoyl glycinate (SCG)) whereas example 7 demonstrates synthesis of same 'super-mild' surfactants in the ratio of 1:1.

Figure 2:
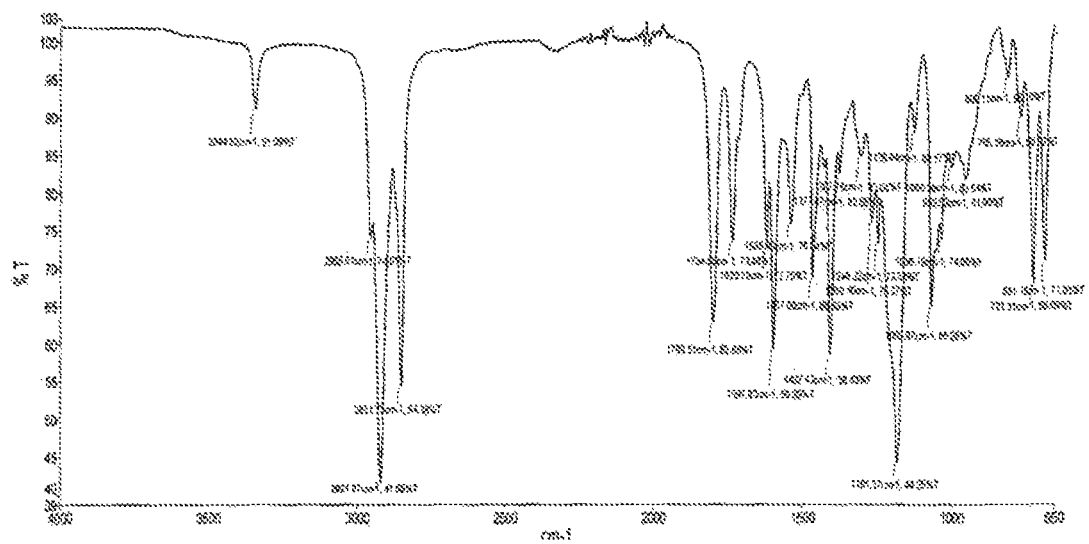
FIG. 2 shows the infrared spectrum of the dried sample of Example 1 with blend of SCI:SCG in a ratio of 1:2 showed carbonyl and NH stretch of amide linkage of N-acyl glycinate at 1605, 1620 cm-1 and at 3344 cm-1 respectively

The infrared spectrum (FIG. 2) of the dried sample of Example 1 with blend of SCI:SCG in a ratio of 1:2 showed carbonyl and NH stretch of amide linkage of N-acyl glycinate at 1605, 1620 cm$^{-1}$ and at 3344 cm$^{-1}$ respectively. The carbonyl of O-acyl isethionate (carbonyl of ester) appeared at 1734 cm$^{-1}$ and, CH stretch of alkyl chains of both mild surfactants appeared at 2850, 2920, and 2956 cm$^{-1}$.

The fatty acid chlorides used in this invention are prepared by the eco-friendly catalytic process reported by Koshti et al. in their recently filed patent application (PCT/IB2012/055197)

Examples 1 to 10 illustrate formation of blend of O-acyl isethionate and N-acyl amino acid surfactants using different fatty acid chlorides.

The alkyl chain represented by R in the fatty acid chloride of Scheme 1 can be even numbered or odd numbered, linear or branched chains. It can be a single chain or a mixture of several alkyl chains ranging from C 5 to C 21. The alkyl chain can be completely saturated or it can be unsaturated with one or more double bonds. These alkyl chain are derived from fatty acids that occur in nature, mostly, in the form of animal fats or vegetable oil. Unsaturated alkyl chains can be derived from oleic acid, recinoleic acid, linolic acid, linolenic acid, eleoosteric acid, eicosenoic acid, euricic acid, docosodienoic acid and undecylenic acid. The saturated fatty acids are usually derived from palm/palm kernel oil or coconut oil and are all even numbered ranging from octanoic acid (C8) to stearic acid (C18). Fatty acids with higher number of carbons (C18 to C22) are derived from mustard oil, tung oil and rapeseed oil. Typical cocoyl chloride composition that was used (Example 1, 3, 5, 6, 7 & 9) to illustrate this invention is given below in Table 1. Example 4 is shown with another grade of cocoyl chloride that has higher percentage of stearoyl chloride.

TABLE 1

| C-Chain Distribution | Specifications |
| --- | --- |
| $C_8$ | 4-12% |
| $C_{10}$ | 4-14% |
| $C_{12}$ | 59-65% |
| $C_{14}$ | 14-24% |
| $C_{16}$ | 1-8% |
| $C_{18}$ | max. 0.5% |

The composition of lauroyl chloride (Example 2 & 8) that was used to illustrate this invention is given in Table 2

TABLE 2

| C-Chain Distribution | Specifications |
| --- | --- |
| $C_8$ | 4-8% |
| $C_{10}$ | 4-8% |
| $C_{12}$ | 80 to 95% |

According to the present invention the types of amino acids that are used in the synthesis of compounds of Formula II in the second step of the process are naturally occurring α-amino acids (Glycine, Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Aspergine, Glutamine), unnatural amino acids (opposite enantiomers having 'D' stereochemistry), mixtures of stereoisomers, unnatural amino acids (amino propionic acid, N-methyl taurine, Sarcosine). In short, the amino acids required for the synthesis of compounds of Formula II need to have either a primary or a secondary amino group at one end and an acid group, either carboxylic or sulphonic at the other end. The present invention is illustrated with amino acid like glycine (primary amino acid with carboxylic group, Example 1 to 4, 7 and 8), N-methyl taurine (secondary amino acid with sulphonic acid group, Example 5) and sarcosine (secondary amino group with carboxylic group, Example 6). Example 9 demonstrates that all three amino acids can be used together to get blend of all three N-acyl amino acid surfactants along with O-acyl isethionates.

The bases for the second step of Schotten Baumann reaction can be selected from hydroxides or carbonates of potassium, sodium or ammonium hydroxide. Water-soluble tertiary amine such as trimethyl or triethyl amine or triethanol amine can also be used in form aqueous solution to create the N-acyl amino acid surfactants of Formula II. Example 3 depicts the use of potassium hydroxide as base whereas all other examples use sodium, hydroxide as the base for Schotten Baumann N-acylation of amino acids.

In the first step of present invention where fatty acid chloride is reacted with hydroxyl ethyl sulphonate to synthesize compound of Formula I, it is likely that some amount of ester-mixed anhydride species (Formula III) can be generated as depicted in Scheme II. The formation of ester-mixed anhydride species may occur in substantial amount due to accidental overrun of the first step where fatty acid chloride is reacted with alkali salt of isethionate. However, during the second step when the resultant flowable pasty mass is reacted with aqueous solutions of amino acids the nucleophile primary amino or secondary amino group preferentially reacts with highly activated anhydride group of compounds of Formula III resulting in the originally desired ratio of compounds of Formula I and compounds of Formula II as shown in Scheme II.

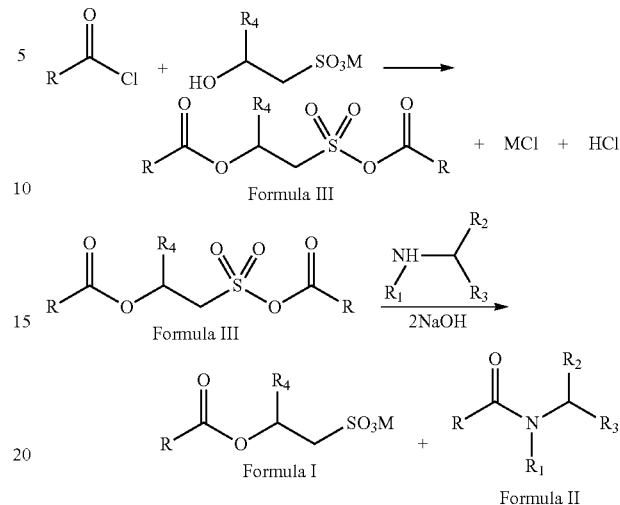

Scheme-II

Thus, Examples 1 to 11 illustrate formation of blends of O-acyl isethionate and N-acyl amino acid surfactants in varying molar ratio using different grades fatty acid chlorides with a variety of different amino acids and bases. The clear blends of O-acyl isethionate and N-acyl amino acid surfactants can be spray dried and a homogenous powder is obtained. On dissolution of this spray dried powder of these two types of surfactants in water with the original solids level results in clear solution with the same chemical analysis. Thus, the blend of super-mild surfactants in the dry form can be easily obtained by routine spray-drying operation. Super-mild blends in the solid form may be desired in certain applications where water is to be avoided. For example, unlike facial cleanser or body washes where aqueous solution of super-mild surfactants can be easily incorporated but in syndet bar cake, addition of aqueous solution of super-mild surfactants would necessarily involve removal of water from the entire mass before extruding and that would be an impossible operation to perform in sigma mixture with heat and vacuum. In such cases dry form of mild surfactant would be needed either in the form of powder or granules or prill.

Example 12 demonstrates that the aqueous blends of O-acyl isethionate and N-acyl amino acid surfactants of this patent application can be dried and conveniently converted into dry form.

Advantages of the Invention

1) Cost-effective & efficient way of manufacturing the 'super-mild surfactant systems' made up of O-acyl isethionate and N-acyl amino acid surfactants.
2) The manufacturing process described in this patent application circumvents many disadvantages associated with traditional energy-intensive esterification DEFI process (high temperature >200° C.) of fatty acid with alkali metal salt of hydroxyl ethyl sulphonates to afford O-acyl isethionates. The direct very high temperature esterification process of fatty acid not only involves very high temperatures but uses excess of fatty acid in stoichiometric quantities. This large excess of stoichiometric quantities need to be removed at the end of the reaction resulting into longer batch cycle time and consumption of energy. Another biggest disadvantage of the high temperature process is that during the recovery of fatty acid, the lower fatty acids get removed due to some degree of transesterification and hence in case of mixture of fatty acid the final composition of O-acyl isethionate product is different than input alkyl chain distribution of fatty acid. The process described in the present application also circumvents another unit operation that necessitates the use of sophisticated equipment to convert molten alkali metal salt of O-acyl isethionate (the product) into powder, granules/prills or needles.

3) O-acylation and N-acylation of alkali metal or ammonium salts of hydroxylalkyl sulphonate and amino acid respectively with fatty acid chloride are done in 4 to 5 hours time with temperatures never exceeding 70° C.

4) Manufacture of 'super-mild' surfactant systems comprising O-acyl isethionates (Formula I) and N-acyl amino acid surfactants (Formula II) in the molar ratio of 1.0:0.5 to 1.0:10 from the same starting raw material which is fatty acid chloride.

5) Manufacture of super mild surfactant systems comprising O-acyl isethionates and N-acyl amino acid surfactants in molar ratio of 1.0:0.5 to 1.0:10 wherein N-acyl amino acid surfactant can be one or more than one. Additionally, one can exploit synergy of acyl isethionates with a mixture of corresponding N-acyl amino acid surfactants like glycinate, taurate or sarcosinate etc.

6) O-acyl isethionates commercially are available in the solid form and N-acyl amino acid surfactants are available in the solid as well as aqueous form. The solid form of O-acyl isethionates is difficult to solubilize in the presence of amino acid surfactants alone and hence there have been several systems reported in literature and commercially products are available as 'liquid carrier systems' of O-acyl isethionates wherein other surfactants like betaines, amphoacetates and sulphosuccinates have been used. However, with the methodology of the present patent application it is possible to create liquid delivery system of O-acyl isethionates with only N-acyl amino acid surfactants and without aid of any third surfactant. It should be noted that O-acyl isethionates (Formula I) and N-acyl amino acid surfactants (Formula II) are the core of 'super-mild' cleansing systems.

7) Blends of 'super-mild' surfactants with O-acyl isethionate and N-acyl amino acid surfactants in dried form can be obtained from the aqueous solutions of the same described in this patent application. Solid dried form of 'super-mild' surfactants is needed for certain skin care applications, for example syndet bars or any other application/use where a solid blend of these two classes of 'super-mild' surfactants can be envisaged where one needs to avoid or use minimal quantity of water (non-aqueous environment).

EXAMPLES

The present invention is now described by way of working on limiting illustrative examples. The detail of the invention provided in the following examples is given by the way of illustration only and should not be construed to limit the scope of the present invention.

Fatty acids were procured from Natural Oleo-chemicals, Malaysia whereas thionyl chloride from Transpek Industries, Vadodara, India. Glycine, sarcosine, and N-methyl taurine were procured from Sigma-Aldrich Fatty acids chlorides were prepared as per the procedure reported in the Patent Application (PCT/IB2012/055197) by Koshti et al. (*Method to produce N-acyl amino acid surfactants using N-acyl amino acid surfactants or corresponding anhydrides as catalyst*).

Anionic activity of the blends of this invention was estimated as per the two phase titration given in the literature. (Introduction to Surfactant Analysis by D C Cullum, Pg 59 to 61 1994, Publisher—Blackie Academic & Professional (Chapman & Hall)

Example 1

Synthesis of a Blend of Sodium Cocoyl Isethionate and Sodium Cocoyl Glycinate (1:2)

The cocoyl chloride used in this experiment had the following alkyl chain distribution

C8: 5.0%
C10: 6.0%
C 12: 63%
C14: 20%
C 16: 6%
C18: 0.4%

To a stirred cocoyl chloride (234 g, 1.05 gmol) under slow purging of nitrogen at room temperature, sodium isethionate (52 g, 0.35 gmol) was added and the slurry was stirred at 55-60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 $cm^{-1}$), sodium cocoyl isethionate (carbonyl of ester at 1734 $cm^{-1}$) and disappearance of hydroxyl stretch (3323 $cm^{-1}$) of sodium isethionate.

This fluid viscous reaction mass (270 g) was cooled to room temperature and then added slowly to a stirred aqueous solution of glycine (53.55 g, 0.71 gmol) in water (730 g) along with sodium hydroxide solution (48.8%, 0.116 g, 1.41 gmol) simultaneously while maintaining the pH of the reaction mass between 10.2 to 10.5 and the temperature between 20 to 30° C. The addition was completed in two hours and the reaction mass was stirred for another 4 h at 25° C. The pH was adjusted to 7.5 with HCl. The solids content of the reaction mass was adjusted to 30% solids content to yield 1169 g of aqueous solution product.

IR spectrum of dried sample showed carbonyl stretch of amide at 1600-1620 $cm^{-1}$ and NH stretch at 3344 $cm^{-1}$. The other significant stretching frequencies were carbonyl of ester of alkanoyl isethionate at 1734 $cm^{-1}$ and total disappearance of carbonyl stretching frequency (1800 $cm^{-1}$) of cocoyl chloride. The analysis of the above aqueous surfactant blend was as follows

| Test | Results |
|---|---|
| Appearance | Light yellow clear liquid |
| Viscosity at 25° C. | 400 cps |
| pH as such | 7.5 |
| NaCl, % w/w | 3.7 |
| Total solids, % w/w | 31.00 |
| Cocoyl isethionate % w/w | 8.40 |
| Sodium cocoyl glycinate % w/w | 14.0 |

Example 2

Synthesis of a Blend of Sodium Lauroyl Isethionate and Sodium Lauroyl Glycinate (1:2)

The lauroyl chloride used in this experiment had the following alkyl chain distribution
C8: 5.0%
C10: 5.0%
C 12: 90%

To a stirred lauroyl chloride (228 g, 1.04 gmol) under slow purging of nitrogen at room temperature, sodium isethionate (52.0 g, 0.35 gmol) was added and the slurry was stirred at 65-70° C. for 4 h. The HCl gas generated was absorbed in alkali solution and the progress of reaction was monitored by IR spectrum analysis. The FTIR spectrum of the intermediate showed the presence of unreacted lauroyl chloride (carbonyl stretch at 1800 cm$^{-1}$), sodium lauroyl isethionate (carbonyl of ester at 1734 cm$^{-1}$) and disappearance of hydroxyl stretch (3323 cm$^{-1}$) of sodium isethionate.

This fluid viscous reaction mass (260 g) was cooled to room temperature and then added slowly to a stirred aqueous solution of glycine (53.5 g, 0.71 gmol) in water (709 g) along with sodium hydroxide solution (48.8%, 116 g, 1.41 gmol) simultaneously while maintaining the pH of the reaction mass between 10 to 10.5 and the temperature between 20 to 30° C. The addition was completed in three hours and the reaction mass was stirred for another 4 h at room temperature of 30° C. The pH was adjusted to 7.5 with a few drops of HCl. The solids content of the reaction mass adjusted to 30% solids content to yield 1138 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester of alkanoyl isethionate at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity at 25° C. | 1400 cps |
| pH as such | 7.54 |
| NaCl, % w/w | 3.5 |
| Total solids, % w/w | 30.4 |
| Sod lauroyl isethionate % w/w | 8.2 |
| Sodium lauroyl glycinate % w/w | 14.0 |

Example 3

Synthesis of a Blend of Potassium Cocoyl Isethionate and Potassium Cocoyl Glycinate (1:2)

The cocoyl chloride used in this experiment had the following alkyl chain distribution
C8: 5.0%
C10: 6.0%
C 12: 63%
C14: 20%
C 16: 6%
C18: 0.4%

To a stirred cocoyl chloride (234.5 g, 1.05 gmol) under slow purging of nitrogen at room temperature, potassium isethionate (57.4 g, 0.35 gmol) was added and the slurry was stirred at 50-55° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of potassium isethionate.

This fluid viscous reaction mass (270 g) was cooled to room temperature and then added slowly to a stirred aqueous solution of glycine (53.55 g, 0.71 gmol) in water (757 g) along with potassium hydroxide solution (50%, 160 g, 1.41 gmol) simultaneously while maintaining the pH of the reaction mass between 10 to 10.5 and the temperature between 20 to 30° C. The addition was completed in three hours and the reaction mass was stirred for another 4 h at 30° C. The pH was adjusted to 7.5 with a few drops of HCl. The solids content of the reaction mass adjusted to 30% solids content to yield 1239 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester of alkanoyl isethionate at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | 300 cps |
| pH | 7.5 |
| KCl, % w/w | 4.58 |
| Total solids, % w/w | 30.9 |
| Potassium cocoyl isethionate % w/w | 7.6 |
| Potassium cocoyl glycinate % w/w | 14.2 |

Example 4

Synthesis of a Blend of Sodium Cocoyl Isethionate and Sodium Cocoyl Glycinate (1:2)

The cocoyl chloride used in this experiment is with higher percentage of long chain fatty acid chloride, namely, palmitoyl chloride and stearoyl chloride had the following alkyl chain distribution
C8: 6.1%
C10: 6.2%
C 12: 58.5%
C14: 19.5%
C 16: 6.5.%
C18: 3.2%

To a stirred cocoyl chloride (236 g, 1.05 gmol (MW 221) under slow purging of nitrogen at room temperature, sodium isethionate (52 g, 0.35 gmol) was added and the slurry was stirred at 55-60° C. for 3.5 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This fluid viscous reaction mass (265 g) was cooled to room temperature and then added slowly to a stirred aqueous solution of glycine (53.55 g, 0.71 gmol) in water (720 g) along with sodium hydroxide solution (48%, 116 g, 1.41 gmol) simultaneously while maintaining the pH of the reaction mass between 10 to 10.5 and the temperature between 20 to 30° C. The addition was completed in three hours and the reaction mass was stirred for another 4 h at 25° C. The pH was adjusted to 7.5 with a few drops of HCl. The solids content of the reaction mass adjusted to 30% solids content to yield 1154 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester of alkanoyl isethionate at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | 1000 Cps |
| pH as such | 7.5 |
| NaCl, % w/w | 3.9 |
| Total solids, % w/w | 30.6 |
| Cocoyl isethionate % w/w | 8.20 |

Example 5

Synthesis of a Blend of Sodium Cocoyl Isethionate and Sodium N-Cocoyl, N-Methyl Taurate (1:2)

The cocoyl chloride used in this experiment had the following alkyl chain distribution
C8: 5.0%
C10: 6.0%
C 12: 63%
C14: 20%
C 16: 6%
C18: 0.4%

To a stirred cocoyl chloride (234 g, 1.05 gmol) under slow purging of nitrogen at room temperature, sodium isethionate (52 g, 0.35 gmol) was added and the slurry was stirred at 60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This pasty reaction mass (260 g) was cooled to room temperature and then added slowly to a stirred aqueous solution of N-methyl taurine (99.246 g, 0.714 gmol) in water (805 g) along with sodium hydroxide solution (48.8% 116 g, 1.414 gmol) simultaneously while maintaining the pH of the reaction mass between 10 to 10.5 and the temperature between 20 to 30° C. The addition was completed in three hours and the reaction mass was stirred for another 4 h at 25° C. The pH was adjusted to 7.5 with a few drops of HCl. The solids content of the reaction mass adjusted to 30% solids content to yield 1280 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | 50 Cps |
| pH as such. | 7.4 |
| NaCl, % w/w | 3.3 |
| Total solids, % w/w | 29.8 |
| Total anionic active matter (sod cocoyl isethionate and sodium cocoyl taurate) % w/w | 22.24 |

Example 6

Synthesis of a Blend of Sodium Cocoyl Isethionate and Sodium N-Cocoyl Sarcosinate (1:2)

The cocoyl chloride used in this experiment had the following alkyl chain distribution
C8: 5.0%
C10: 6.0%
C 12: 63%
C14: 20%
C 16: 6%
C18: 0.4%

To a stirred cocoyl chloride (234 g, 1.05 gmol) under slow purging of nitrogen at room temperature, sodium isethionate (52 g, 0.35 gmol) was added and the slurry was stirred at 60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This pasty reaction mass (260 g) was cooled to room temperature and then added slowly to a stirred aqueous solution of sodium sarcosine (198 g of 40% aqueous solution, 0.71 gmol) in water (670 g) along with sodium hydroxide solution (48.8% 57.4 g, 0.7 gmol) simultaneously while maintaining the pH of the reaction mass between 10 to 10.5 and the temperature between 20 to 30° C. The addition was completed in three hours and the reaction mass was stirred for another 4 h at 25° C. The pH was adjusted to 7.5 with a few drops of HCl. The solids content of the reaction mass adjusted to 30% solids content to yield 1185 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester at 1734 cm$^{-1}$ and total disappearance of carbonyl stretching frequency (1800 cm$^{-1}$) of cocoyl chloride.

The analysis of the above aqueous surfactant blend was as follows

| Test | Results |
| --- | --- |
| Appearance | Light yellow liquid |
| Viscosity 25° C. | 50 Cps |
| pH as such | 7.5 |
| NaCl, % w/w | 3.40 |
| Total solids % w/w | 30.5 |
| Sod cocoyl isethionate % w/w | 7.22 |
| Sod cocoyl sarcosinate % w/w | 14.4 |

Example 7

Synthesis of a Blend of Sodium Cocoyl Isethionate and Sodium Cocoyl Glycinate (1:1)

The cocoyl chloride used in this experiment had the following alkyl chain distribution.
C8: 5.0%
C10: 6.0%
C 12: 63%
C14: 20%
C 16: 6%
C18: 0.4%

To a stirred cocoyl chloride (223 g, 1.0 gmol) under slow purging of nitrogen at room temperature, sodium isethionate (74.05 g, 0.5 gmol) was added and the slurry was stirred at 55-60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This pasty reaction mass (265 g) was cooled to room temperature and then added slowly to a stirred aqueous solution of glycine (38.25 g, 0.51 gmol) in water (671 g) along with sodium hydroxide solution (48.8%, 83 g, 1.01 gmol) simultaneously while maintaining the pH of the reaction mass between 10 to 10.5 and the temperature between 20 to 30° C. The addition was completed in three hours and the reaction mass was stirred for another 4 h at 30° C. The solids content of the reaction mass adjusted to 30% solids content to yield 1057 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | 1320 cps |
| pH as such | 7.5 |
| NaCl, % w/w | 3.20 |
| Total solids, % w/w | 30.5 |
| Sod cocoyl isethionate % w/w | 11.45 |
| Sodium cocoyl glycinate %, w/w | 10.5 |

Example 8

Synthesis of a Blend of Sodium Lauroyl Isethionate and Sodium Lauroyl Glycinate (1:1)

The lauroyl chloride used in this experiment had the following alkyl chain distribution
C8: 5.0%
C10: 5.0%
C 12: 90%

To a stirred lauroyl chloride (217.47 g, 1.00 gmol) under slow purging of nitrogen at room temperature, sodium isethionate (74.05 g, 0. gmol) was added and the slurry was stirred at 65-70° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This fluid viscous reaction mass (265 g) was cooled to room temperature and then added slowly to a stirred aqueous solution of glycine (38.25 g, 0.71 gmol) in water (671 g) along with sodium hydroxide solution (48.8%, 82.78 g, 1.01 gmol) simultaneously while maintaining the pH of the reaction mass between 10.0 to 10.5 and the temperature between 20 to 30° C. The addition was completed in three hours and the reaction mass was stirred for another 4 h at 30° C. The pH was adjusted to 7.5 with a few drops of HCl. The solids content of the reaction mass adjusted to 30% solids content to yield 1057 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester of alkanoyl isethionate at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | Pasty |
| pH as such | 7.5 |
| NaCl, % w/w | 2.9 |
| Total solids, % w/w | 29.5 |
| Sod lauroyl isethionate % w/w | 9.82 |
| Sodium lauroyl glycinate % w/w | 13.0 |

Example 9

Synthesis of a Blend of Sodium Cocoyl Isethionate and Sodium Cocoyl Amino Acid Surfactants:Sodium Cocoyl Isethionate:(Sodium Cocoyl Glycinate, Sodium Cocoyl Sarcosinate and Sodium Cocoyl Taurate):1:2

The cocoyl chloride used in this experiment had the following alkyl chain distribution
C8: 5.0%
C10: 6.0%
C 12: 63%
C14: 20%
C 16: 6%
C18: 0.4%

To a stirred cocoyl chloride (234 g, 1.05 gmol) under slow purging of nitrogen at room temperature, sodium isethionate (52 g, 0.35 gmol) was added and the slurry was stirred at 55-60° C. for 4 h. The HCl gas generated was absorbed in, alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This fluid viscous reaction mass (260 g) was cooled to room temperature and then added slowly to a stirred aqueous solution of glycine (17.5 g, 0.23 gmol), N-methyl taurine (32.5 g, 0.23 gmol) and sarcosine (65 g, of 40% aqueous solution, 0.23 mol) in water (706 g) along with sodium hydroxide solution (48.5%, 95.63 g, 1.16 gmol) simultaneously while maintaining the pH of the reaction mass between 10 to 10.5 and the temperature between 20 to 30° C. The addition was completed in two hours and the reaction mass was stirred for another 4 h at 25° C. The pH was adjusted to 7.5 with a few drops of HCl. The solids content of the reaction mass adjusted to 30% solids content to yield 1176 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester of alkanoyl isethionate at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity at 25° C. | 50 cps |
| pH as such | 7.5 |
| NaCl, % w/w | 3.6 |
| Total solids, % w/w | 30.80 |
| Cocoyl isethionate and taurate % w/w | 13.00 |
| Sodium cocoyl glycinate and sodium cocoyl sarcosinate % w/w | 10.0 |

Example 10

Synthesis of a Blend of Sodium Cocoyl Isethionate and Sodium N-Cocoyl, N-Methyl Taurate (1:2) with Solids Content of 35% w/w The cocoyl chloride used in this experiment had the following alkyl chain distribution
C8: 5.0%
C10: 6.0%
C 12: 63%
C14: 20%
C 16: 6%
C18: 0.4%

To a stirred cocoyl chloride (234 g, 1.05 gmol) under slow purging of nitrogen at room temperature, sodium isethionate (52 g, 0.35 gmol) was added and the slurry was stirred at 60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This pasty reaction mass (260 g) was cooled to room temperature and then added slowly to a stirred aqueous solution of N-methyl taurine (99.246 g, 0.714 gmol) in water (696 g) along with sodium hydroxide solution (48.8% 116 g, 1.414 gmol) simultaneously while maintaining the pH of the reaction mass between 10 to 10.5 and the temperature between 20 to 30° C. The addition was completed in three hours and the reaction mass was stirred for another 4 h at 25° C. The pH was adjusted to 7.5 with a few drops of HCl. The solids content of the reaction mass adjusted to 35% solids content to yield 1171 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | 50 Cps |
| pH as such | 7.54 |
| NaCl, % w/w | 3.62 |
| Total solids, % w/w | 35.30 |
| Total anionic active matter (sod cocoyl isethionate and sodium cocoyl taurate) % w/w | 24.60 |

Example 11

Synthesis of a Blend of Sodium Cocoyl Isethionate and Sodium N-Cocoyl, N-Methyl Taurate (1:2) with Solids Content of 40% w/w The cocoyl chloride used in this experiment had the following alkyl chain distribution
C8: 5.0%
C10: 6.0%
C 12: 63%
C14: 20%
C 16: 6%
C18: 0.4%

To a stirred cocoyl chloride (234 g, 1.05 gmol) under slow purging of nitrogen at room temperature, sodium isethionate (52 g, 0.35 gmol) was added and the slurry was stirred at 60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 cm$^{-1}$), sodium cocoyl isethionate (carbonyl of ester at 1734 cm$^{-1}$) and disappearance of hydroxyl stretch (3323 cm$^{-1}$) of sodium isethionate.

This pasty reaction mass (260 g) was cooled to room temperature and then added slowly to a stirred aqueous solution of N-methyl taurine (99.246 g, 0.714 gmol) in water (560 g) along with sodium hydroxide solution (48.8% 116 g, 1.414 gmol) simultaneously while maintaining the pH of the reaction mass between 10 to 10.5 and the temperature between 20 to 30° C. The addition was completed in three hours and the reaction mass was stirred for another 4 h at 25° C. The pH was adjusted to 7.5 with a few drops of HCl. The solids content of the reaction mass adjusted to 40% solids content to yield 1034 g of aqueous solution product.

IR spectrum of dried sample showed carbonyl stretch of amide at 1600-1620 cm$^{-1}$ and NH stretch at 3344 cm$^{-1}$. The other significant stretching frequencies were carbonyl of ester at 1734 cm$^{-1}$ and total disappearance of carbonyl stretching frequency (1800 cm$^{-1}$) of cocoyl chloride. The analysis of the above aqueous surfactant blend was as follows

| Test | Results |
| --- | --- |
| Appearance | Light yellow clear liquid |
| Viscosity 25° C. | 550 Cps |
| pH as such | 7.55 |
| NaCl, % w/w | 4.80 |
| Total solids, % w/w | 40.0 |
| Total anionic active matter (sod cocoyl isethionate and sodium cocoyl taurate) % w/w | 30.1. |

Example 12

Conversion of the Aqueous Blend of Example 1 (Sodium Cocoyl Isethionate and Sodium N-Cocoyl Glycinate (1:2)) into Powder The aqueous solution of Example 1 was sprayed by nitrogen and the atomized particles were dried by hot air of 180° C. (inlet temperature) and 100° C. (outlet temperature) in laboratory spray-dryer at the feed rate of 200 ml/h.

The fine powder exhibited the particle size distribution 80% between mesh size of 60-200, 10% above 200 mesh size and 10% below 60 mesh size.

The powder was re-dissolved to give an aqueous solution with 30% solids content

| Test | Results |
| --- | --- |
| Appearance | Light yellow clear liquid |
| Viscosity at 25° C. | 400 cps |
| pH as such | 7.5 |
| NaCl, % w/w | 3.7 |
| Total solids, % w/w | 30.20 |
| Cocoyl isethionate % w/w | 8.30 |
| Sodium cocoyl glycinate % w/w | 14.0 |

We claim:

1. A process of producing an aqueous blend of an O-acyl isethionate of Formula I, and an N-acyl amino acid based surfactant of Formula II,

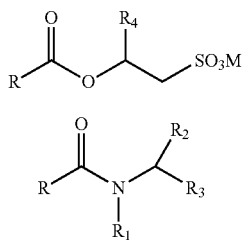

Formula I

Formula II wherein:

R is selected from the group consisting of saturated and unsaturated $C_5$ to $C_{21}$ alkyl groups, $R_1$ is selected from the group consisting of H and $C_1$ to $C_4$ alkyl, $R_2$ is hydrogen, or $R_2$ is an organic group having a structure which corresponds to a side chain bound to an α-carbon of a naturally occurring α-amino acid, $R_3$ is selected from the group consisting of COOX and $CH_2.SO_3X$, where X is selected from the group consisting of $Li^+$, $Na^+$ and $K^+$, R4 is selected from the group consisting of H and methyl, and M is a cation selected from $Na^+$, $K^+$, $NH_4^+$, and a quaternary ammonium cation derived from a tertiary amine, said method comprising:

A) reacting more than one equivalent of a fatty acid chloride with alkali metal or ammonium salts of a hydroxyalkyl sulphonate to obtain a compound of Formula I, and B) reacting unreacted fatty acid chloride in the product of step (A) with an amino acid reactant in the presence of a base under aqueous Schotten Baumann reaction conditions to yield compounds of Formula II.

2. The process as claimed in claim 1, wherein the temperature of step (A) is between 50° C. and 70° C.

3. The process as claimed in claim 1, wherein the pH of step (B) is maintained between 9 and 10.5.

4. The process as claimed in claim 1, wherein the temperature of step (B) is less than 50° C.

5. The process as claimed in claim 1, wherein the amino acid reactant is selected from the group consisting of naturally occurring α-amino acids and non-naturally occurring amino acids.

6. The process as claimed in claim 5, wherein the amino acid reactant is selected from the group consisting of Glycine, Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Aspergine and Glutamine.

7. The process as claimed in claim 5, wherein the amino acid reactant is a stereoisomer of a naturally occurring α-amino acid having D stereo chemistry, amino propionic acid, N-methyl taurine, or sarcosine.

8. The method of claim 1, further comprising a step of spray drying the product of step (B) to obtain a solid blend of said O-acyl isethionate of Formula I and said N-acyl amino acid based surfactant of Formula II.

* * * * *